United States Patent [19]

Barua et al.

[11] Patent Number: 4,473,503

[45] Date of Patent: Sep. 25, 1984

[54] 15-FLUORO-RETINOID COMPOUNDS

[75] Inventors: Arun B. Barua; James A. Olson, both of Ames, Iowa

[73] Assignee: Iowa State University Research Foundation, Inc., Ames, Iowa

[21] Appl. No.: 443,940

[22] Filed: Nov. 23, 1982

Related U.S. Application Data

[63] Continuation-in-part of Ser. No. 359,110, Mar. 17, 1982.

[51] Int. Cl.³ .............................................. C07C 57/70
[52] U.S. Cl. ..................................... 260/408; 570/131
[58] Field of Search ........................... 260/544 F, 408; 570/131

[56] References Cited

U.S. PATENT DOCUMENTS 3,281,440 10/1966 Machleidt et al. .................. 568/824
4,055,659 10/1977 Gander et al. ...................... 424/305

OTHER PUBLICATIONS

Barua, Arun B. et al., *Biochimica et Biophysica Acta*, vol. 757, (1983), pp. 288–295.
Dawson, Marcia I. et al., *Carbohydrate Research*, vol. 85, (1980), pp. 121–129.
Hicks, R. Marian, *Proc. Nutr. Soc.*, vol. 42, (1983), pp. 83–84.
Kirk–Othmer, *Encyclopedia of Chemical Technology*, 2nd Ed. vol. I, (1963), pp. 222–223.
Clark, N. G., *Modern Organic Chemistry*, (1964), Oxford Univ. Press at p. 153.

*Primary Examiner*—Natalie Trousof
*Assistant Examiner*—L. Hendriksen

[57] ABSTRACT

This invention relates to the 15-fluoro-retinoid compounds which provide vitamin A activity with reduced liver storage. A preferred compound is retinoyl fluoride.

2 Claims, No Drawings

15-FLUORO-RETINOID COMPOUNDS

RELATED APPLICATION

This application is a continuation-in-part of co-pending application Ser. No. 359,110, filed Mar. 17, 1982.

GRANT REFERENCE

The invention described herein was made in the course of work under two grants from the USDA: CSRS grant No. 616-15-173 and competitive grant No. 5901-0410-8-0011.

BACKGROUND AND PRIOR ART

The 10-, 12-, 14- and 20-fluororetinoic acids and the 10-, 12- and 12,20-difluororetinoic acids have been reported in the literature: Machleidt et al, *Justus Liebigs Ann. Chem.*, 1964, 674: 1; ibid, 1964, 679: 20; ibid, 1965, 681: 21 and U.S. Pat. No. 3,281,440. These compounds were found to have hypocholesterolemic activity. The 10- and 14- fluororetinals were synthesized in 1978 (Asato et al., *J. Am. Chem. Soc.*, 1978, 100: 5957) and were shown to form fluorinated rhodopsin analogs.

The biological activities of the methyl and ethyl esters of 10-, 12- and 14-fluororetinoic acids have been evaluated in a chemically induced mouse papilloma test, and antipapilloma activity greater than the parent non-fluorinated esters were found for ethyl 12-fluororetinoate (Pawson et al., *J. Med. Chem.*, 1979, 22: 1059–1067). Pawson et al have also synthesized (4-methoxy-2, 3,6-trimethylphenyl) nonatetraenoic acids, esters and amides (analogs of retinoic acid) bearing fluorine or the trifluoromethyl group on the polyene side chain (*J. Med. Chem.*, 1979, 22: 1059–1067; ibid, 1981, 24: 101–104), and reported studies of antipapilloma activity.

The use of retinoic acid clinically against dermatoses was reported in 1959, and since that time it has been used in the treatment of acne, psoriasis, ichthyosiform dermatoses, dyskeratoses and various other skin diseases. See *The Therapeutic Use of Vitamin A Acid*, Proceedings of the International Symposium, Films, Switzerland, Jan. 27–29, 1975; and Acta Dermato-Venereologica, 1975, 55 (Supplement 74), 11–185.

Dietary vitamin A is required for growth, epithelial cell differentiation, vision and reproduction. The mechanism of action of vitamin A in vision is rather well defined, and either retinol or retinal, which are biologically interconvertible, can support vision. Retinoic acid, a natural biological metabolite of retinol, possesses equal growth promoting activity as retinol, but is not active in supporting vision or reproduction. No reports are available on the synthesis of N-retinoyl amino acids.

SUMMARY OF INVENTION

This invention provides a class of novel retinoid compounds having vitamin A activity while at the same time providing markedly reduced liver storage. Therefore, even though the level of vitamin A activity is somewhat less than retinol (vitamin A) or retinoic acid (vitamin A analog), the finding that the storage of the fluoro-substituted compounds of this invention in the liver is much less than with retinol or retinoic acid provides an important advantage in the oral administration of vitamin A activity for therapeutic purposes.

The compounds of this invention are characterized by having from 1 to 2 fluorines bonded to the C-15 carbon of retinol or retinoic acid. For example, the hydroxyl group of C-15 acid group of retinoic acid may be replaced with fluorine. Similarly, the C-15 end group of retinol may be modified by replacing both one of the hydrogens and also the hydroxyl group with fluorine.

DETAILED DESCRIPTION

The 15-fluoro-retinoid compounds of this invention can be represented by the following molecular formula:

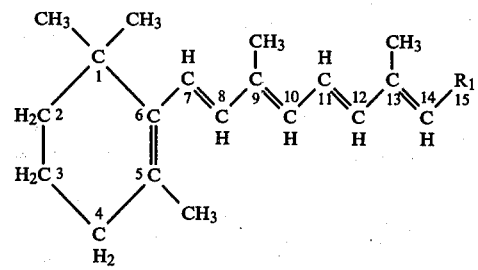

wherein $R_1$ group, representing a C-15 group, has from 1 to 2 fluorines bonded to the C-15 carbon. For example, in the preferred C-15 fluoro derivatives, $R_1$ is represented by one of the following groups:

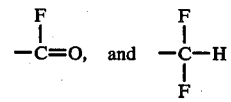

wherein F,C,O, and H are respectively fluorine, carbon, oxygen, and hydrogen. For example, the compounds of this invention include retinoyl fluoride and 15, 15-difluoroaxerophthene.

A useful fluorinating agent for preparing the compounds of the present invention is a N-diethylaminosulfurtrifluoride (DAST). The DAST reagent can be prepared by the method of L. N. Markovski et al., 1973, Synthesis, p. 787, or obtained commercially from Aldrich Chemical Co. It has been found that retinoic acid reacts readily with the DAST reagent to produce retinoyl fluoride in high yield. DAST also reacts with retinal to produce 15,15-difluoroaxerophthene.

Retinoyl fluoride, unlike most acyl chlorides, is stable in aqueous solution for several days and is hydrolyzed to retinoic acid only on heating in the presence of alkali or acid. It is not appreciably hydrolyzed to retinoic acid even in the presence of bicarbonate at 35°–40° C.

Retinoyl fluoride can be used as a starting material for the preparation of a new series of compounds, viz. N-retinoyl derivatives of glycine or other α-amino acids. In general, retinoyl fluoride will react with compounds containing a free $NH_2$ group. The C-15 carbon of the retinyl moiety is bonded to the amino nitrogen. The general structure is as follows:

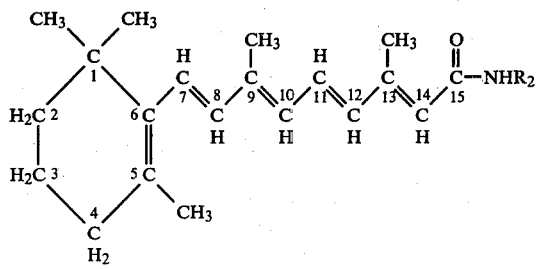

wherein $R_2$ is the carboxylic acid portion of the 60-amino acid.

Retinoyl fluoride has 22–36% of the biological activity of all-trans retinyl acetate by rat growth bioassay. However neither retinoyl fluoride nor any of its metabolites were found to be stored in appreciable amounts in the liver or other tissues.

EXAMPLE I

Synthesis of Retinoyl Fluoride

Retinoyl fluoride was prepared as follows:

300 Mg of retinoic acid was dissolved in 20 ml of warm diethyl ether. The solution was cooled in ice and 161 mg of N-diethylaminosulfurtrifluoride (DAST) dissolved in 1.0 ml of diethylether was added dropwise. (The DAST was prepared by the method of Markovski et al., 1973, Synthesis, p. 787.) The reaction mixture was warmed to room temperature and the solvent removed in vacuo. The orange residue was dissolved in 2 ml of acetone and immediately applied to three (20×20 cm) plates of silica gel and subjected to thin layer chromatography (t.l.c.) using hexane/diethylether (7:3 v/v) as the solvent mixture.

Retinoyl fluoride, which is orange-yellow in color, separated as the main band ($R_f=0.68$). It was eluted with diethylether, and the solvent removed to give 240 mg of oil. Upon dissolving the oil in the minimum volume of pentane, and storing the solution at $-20°$ C., orange-yellow crystals m.p. 65°–67° C. were obtained: $\lambda_{max}$ 378 nm (hexane), $E_{1cm}^{1\%}=1650$. IR (KBr) 1788 (C=O), 1070 (C-F) cm$^{-1}$. M.S. (m/e) 302 (M+), 287 (M+-15 (CH$_3$)), 282 (M+-20(HF)), 267 (M+-35(OF)), 259, 255 (M+-47(COF)). $^{19}$F NMR (CDCl$_3$) 14.74 ppm downfield from CFCl$_3$. Anal. Calcd. for C$_{20}$H$_{27}$FO: C, 79.46; H, 8.94; F, 6.25. Found: C,79.42; H, 9.08; F, 5.92. NMR (CDCl$_3$), δ1.03 (6H), 1.46 (2H), 1.71 (3H), 2.02 (3H), 2.05 (2H), 2.39/2.40 (3H), 5.73 (1H), 6.12 (1H), 6.17 (1H), 6.29 (1H), 6.34 (1H), 7.11 (1H).

Several other isomers were apparently formed. One of these isomers believed to be the 13-cis retinoyl fluoride showed a $R_f$ on t.l.c. of 0.80 and a $\lambda_{max}$ of 373 nm (hexane). HPLC (Whatman Partisil 10 (Type M9) column; 5% ethylacetate in hexane as the eluant at a rate of 4 ml/min, 370 nm detector) showed the retention time of the all-trans isomer to be 10.5 min and that of the 13-cis isomer to be 7.5 min.

EXAMPLE II

Synthesis of 15,15-Difluoroaxerophthene 15,15-Difluoroaxerophthene was prepared as follows:

100 mg of retinal was dissolved in 2–3 ml of CH$_2$Cl$_2$ in a test tube, and the solvent was removed by passing argon through the solution. The oil was then treated with 56 mg of DAST. The mixture was kept at 80° C. for 30 min in an atmosphere of argon. The mixture was cooled, diluted with 5 ml of diethyl ether and then hydrated with crushed ice. The ether layer was washed with water several times and then dried over Na$_2$SO$_4$. The solvent was removed in vacuo and the red oil was dissolved in 1 ml of acetone. T.L.C. of the solution on silica gel using 4:1 (v/v) hexane-diethyl ether resulted in separation of 15,15-difluoroaxerophthene ($R_f=0.80$) as the major band. 15,15-Difluoroaxerophthene was eluted with diethyl ether and the solvent removed in vacuo to give 60 mg of the compound as an orange-yellow oil.

$\lambda_{max}$ 325 nm, ~390 nm. Mass spectrum: 306 (M+), 286 (M+-20 (HF)), 271 (M+-20-15 (CH$_3$)). $^{19}$F NMR (CDCl$_3$): 35.13 (d, J=19 Hz) ppm upfield from CF$_3$COOH.

In the foregoing Examples, the principal products are believed to be in the form of the all-trans isomers, while the minor products referred to in certain of the Examples are believed to be the 13-cis isomers. However, for the purpose of this invention, both the all-trans, or the 13-cis isomers may be used, or mixtures of the isomers. With respect to other C-15 substituted derivatives, which retain vitamin-A activity, other derivatives disclosed in the literature may be used. See Newton, et al., *Cancer Research*, 1980, 40: 3414–3425.

EXAMPLE III

Preparation of N-Retinoyl Glycine

Glycine (15 mg) was suspended in water (2 ml) to which solid NaHCO$_3$ (15 mg) was added. A solution of retinoyl fluoride was prepared by dissolving 30 mg of retinoyl fluoride in 1 ml diethyl ether; 4 ml of methanol was added to the solution and then the glycine solution. The mixture was stirred at room temperature for 1 hour. The solution was diluted with water and any excess of retinoyl fluoride was extracted with diethyl ether. The yellow aqueous solution was then acidified with acetic acid and the retinoids were extracted with diethyl ether. The yellow extract was washed with water, dried over anhyd. Na$_2$SO$_4$ and then evaporated to dryness in a rotary evaporator. The residual oil was dissolved in acetone and subjected to thin layer chromatography (TLC) on silica gel plates with 2:1 hexane-acetone. Two bands separated, a very small band ($R_f=0.71$) that contained retinoic acid and a major broad band ($R_f=0.47$) that contained N-retinoyl glycine. The compounds were eluted with CH$_2$Cl$_2$ and ether. N-Retinoyl glycine was crystallized from CH$_2$CL$_2$ pentane (1:10) at $-20°$ C. UV $\lambda_{max}$ 345 nm (methanol) which did not change in basic solution. In contrast, the $\lambda_{max}$ of retinoic acid in methanol shifted from 350 nm to 335 nm in presence of base. In the mass spectrum of N-retinoyl glycine, the following ions were prominent: 357 (M+), 339 (M+-18(HOH), 255 (M+-102, CONHCH$_2$COOH).

Following the above procedure and using 1:1 mole of retinoyl fluoride and the appropriate amino acid, the following were prepared:

N-Retinoyl lysine and N-retinoyl tryptophan.

DETERMINATION OF PROPERTIES

1. Determination of Biological Activity

Retinoyl fluoride was tested for vitamin A activity, as compared with retinyl acetate (vitamin A acetate).

The procedure described by Embree et al., Methods in Biochemical Analysis, 1957, p. 43–98 (Ed. D. Glick, Interscience, New York) and recommended by the U.S. Pharmacopeia XIII and XIV was followed.

Rats were made vitamin A-deficient and divided into 5 groups: one group served as control and received no supplement; another two groups received 5 and 10 μg/day/rat of retinoyl fluoride and the remaining two groups received 2 and 4 μg/day/rat of all-trans retinyl acetate. Rats in the control group died before the bioassay was over. The rats in the other four groups resumed growth. The gain in weight of the rats are shown in Table 1. The biological activity of retinoyl fluoride, as compared with retinyl acetate was found to be 22%.

TABLE 1

Biological Activity of Retinoyl Fluoride as Compared with Retinyl Acetate

| Expt. No. | No. of Rats | Compound Dosed | Amount Dosed (μg/rat/day) | Weight Gain (g/wk/rat) | Biological Activity (%) |
|---|---|---|---|---|---|
| | 6 | Retinyl Acetate | 2 | 18.8 | 100 |
| | 6 | | 4 | 27.5 | |
| | 7 | Retinoyl Fluoride | 5 | 15.1 | 22 |
| | 7 | | 10 | 19.8 | |

2. Determination of Liver Storage

Tests were carried out to determine liver retention of retinoyl fluoride using a standard procedure, and comparing the compounds with retinyl acetate (vitamin A acetate). The procedure was as follows:

At the end of the bioassay, the rats receiving 4 μg/day of retinyl acetate were continued on the supplement of retinyl acetate for 5 more days. The rats were then killed and the livers were analyzed for various metabolites of vitamin A by high pressure liquid chromatography (HPLC). The amounts of retinoic acid, retinol and retinyl esters stored in the liver are shown in Table 2.

The rats receiving 10 μg/day of retinoyl fluoride were given, at the end of bioassay, 1 mg/rat of retinoyl fluoride for 5 days. The rats were killed and the liver vitamin A was analyzed by HPLC as in the case of retinyl acetate-dosed rats. The vitamin A analyzed are shown in Table 2.

TABLE 2

Comparison of Liver Storage of Vitamin A by Rats Receiving Retinyl Acetate and Retinoyl Fluoride

| Compound Dosed | Amount Received in 35 days (μg/rat) | Retinoic Acid | Retinol (μg/liver) | Retinyl Esters | Retinoyl Fluoride |
|---|---|---|---|---|---|
| Retinyl Acetate | 140 μg | Not Detected | 1.7 μg | 40.3 μg | Absent |
| Retinoyl Fluoride | 5350 μg | Not Detected | | Not Detected | Detected |

*Retinoic acid is difficult to detect even after massive dose (1 mg or more) of retinoic acid due to its rapid metabolism and excretion. Hence it is necessary to use labelled retinoid to detect retinoic acid. In order to study if retinoic acid was the sole metabolite of retinoyl fluoride, the following experiment was carried out.

METABOLISM OF (11-$^3$H) RETINOYL FLUORIDE

Vitamin A deficient rats receiving retinoyl fluoride for 30 days were dosed with (11-$^3$H) retinoyl fluoride. The rats were divided into 3 groups and killed 1 hour, 3 hour, and 7 days after the dose. The livers were analyzed by HPLC for retinoic acid or other metabolites. The percent of radioactivity recovered from the liver and the metabolites that were present in the liver are shown in Table 3.

TABLE 3

Recovery of Radioactivity from the Livers of Rats Dosed with (11-$^3$H) Retinoyl Fluoride

| Time | Total Radioactivity Recovered | Percent Distribution of Recovered Radioactivity |
|---|---|---|
| 1 hour | 0.10% | Retinoic acid: 18.6%<br>Retinol: Not Detected<br>Retinyl Esters: Not detected<br>Retinoyl Fluoride: Not detected<br>Others (not characterized 81.4% |
| 3 hours | 0.42% | Retinoic acid: 49.6%<br>Retinol: Not Detected<br>Retinyl esters: Not detected<br>Retinoyl Fluoride: Not detected<br>Others: 50.4% |
| 7 days | 0.27% | Retinoic acid: 25.6%<br>Retinol: Not Detected<br>Retinyl esters: Not detected<br>Retinoyl fluoride: Not detected<br>Others: 74.4% |

The above experiment shows that at no time was a significant accumulation of radioactivity noted in the liver. If retinoic acid was the sole metabolite of retinoyl fluoride, the accumulation of radioactivity in the liver after 1 hour and 3 hours should have been much higher (A. M. McCormick et al., *Biochem. J.* 186: 475–481, 1980) and should not have been present on day 7, as retinoic acid is completely metabolized within 48 hours. (H. F. DeLuca, Fed. Proc. 38: 2519–2523, 1979). No toxic side effects were noticed in the rats dosed with retinoyl fluoride (up to 1 mg dose).

We claim:
1. Retinoyl fluoride.
2. The all-trans isomer of retinoyl fluoride.

* * * * *